(12) United States Patent
Ichiki et al.

(10) Patent No.: US 10,397,489 B2
(45) Date of Patent: Aug. 27, 2019

(54) LIGHT SOURCE CONTROL DEVICE, METHOD OF CONTROLLING LIGHT SOURCE, AND IMAGE CAPTURE SYSTEM

(71) Applicant: SONY CORPORATION, Tokyo (JP)

(72) Inventors: Hiroshi Ichiki, Kanagawa (JP); Hisakazu Shiraki, Kanagawa (JP); Yukihiro Nakamura, Kanagawa (JP); Kentaro Fukazawa, Tokyo (JP); Takeshi Miyai, Kanagawa (JP); Kenta Yamaguchi, Kanagawa (JP); Daisuke Kikuchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/572,662

(22) PCT Filed: Mar. 8, 2016

(86) PCT No.: PCT/JP2016/057110
§ 371 (c)(1),
(2) Date: Nov. 8, 2017

(87) PCT Pub. No.: WO2016/185763
PCT Pub. Date: Nov. 24, 2016

(65) Prior Publication Data
US 2018/0139370 A1    May 17, 2018

(30) Foreign Application Priority Data
May 15, 2015   (JP) .................................. 2015-100199

(51) Int. Cl.
*H04N 5/235*    (2006.01)
*H04N 5/04*     (2006.01)
(Continued)

(52) U.S. Cl.
CPC ....... *H04N 5/2354* (2013.01); *A61B 1/00009* (2013.01); *A61B 1/045* (2013.01);
(Continued)

(58) Field of Classification Search
CPC .... A61B 1/04; A61B 1/05; A61B 1/06; A61B 1/0661; G06T 7/90; H04N 5/2354;
(Continued)

(56) References Cited

U.S. PATENT DOCUMENTS 5,834,761 A * 11/1998 Okada .................. G03B 5/00
                                                250/208.1
2003/0063006 A1* 4/2003 Gutta ................. G01N 21/8803
                                                340/603
(Continued)

FOREIGN PATENT DOCUMENTS

JP   2008-73345 A    4/2008
JP   2014-113328 A   6/2014
(Continued)

OTHER PUBLICATIONS

International Search Report dated Jun. 7, 2016 in PCT/JP2016/057110.

*Primary Examiner* — Anner N Holder
(74) *Attorney, Agent, or Firm* — Oblon, McClelland, Maier & Neustadt, L.L.P.

(57) ABSTRACT

[Object] To improve the quality of an acquired image by detecting each piece of color information of red (R), green (G), and blue (B) components to effectively utilize the dynamic range of the image sensor while using a single-plate image sensor.
[Solution] Provided is a light source control device including: a light source control unit configured to cause a plurality of narrowband light sources including at least a red light source, a green light source, and a blue light source to emit
(Continued)

light on a time division basis; and a light quantity setting unit configured to set an output of each of the narrowband light sources on the basis of image information that is frame-sequentially detected by a monochrome single-plate image sensor configured to capture a reflected image of a subject illuminated with light emitted from the narrowband light source.

20 Claims, 13 Drawing Sheets

(51) Int. Cl.
| | |
|---|---|
| H04N 9/73 | (2006.01) |
| H04N 5/225 | (2006.01) |
| G06T 7/90 | (2017.01) |
| A61B 1/05 | (2006.01) |
| A61B 1/06 | (2006.01) |
| H04N 9/04 | (2006.01) |
| A61B 1/00 | (2006.01) |
| A61B 1/045 | (2006.01) |

(52) U.S. Cl.
CPC .............. *A61B 1/05* (2013.01); *A61B 1/0638* (2013.01); *A61B 1/0661* (2013.01); *G06T 7/90* (2017.01); *H04N 9/045* (2013.01); *H04N 9/04521* (2018.08); *H04N 9/735* (2013.01); *H04N 2005/2255* (2013.01)

(58) Field of Classification Search
CPC .......... H04N 2005/2255; H04N 9/045; H04N 9/04521; H04N 9/735
See application file for complete search history.

(56) References Cited

U.S. PATENT DOCUMENTS

| | | | |
|---|---|---|---|
| 2007/0027362 A1* | 2/2007 | Handa | A61B 1/00009 600/160 |
| 2007/0229658 A1* | 10/2007 | Kanamori | G06T 3/40 348/135 |
| 2008/0074492 A1 | 3/2008 | Iwasaki | |
| 2009/0023991 A1* | 1/2009 | Gono | A61B 1/00009 600/109 |
| 2012/0123213 A1* | 5/2012 | Seto | A61B 1/0638 600/178 |
| 2015/0009310 A1* | 1/2015 | Morimoto | A61B 1/05 348/68 |
| 2015/0091447 A1* | 4/2015 | Kubo | A61B 1/045 315/153 |

FOREIGN PATENT DOCUMENTS

| | | |
|---|---|---|
| JP | 2014-183908 A | 10/2014 |
| JP | 2015-66049 A | 4/2015 |
| JP | 2015-66137 A | 4/2015 |
| WO | WO 2015/016172 A1 | 2/2015 |

* cited by examiner

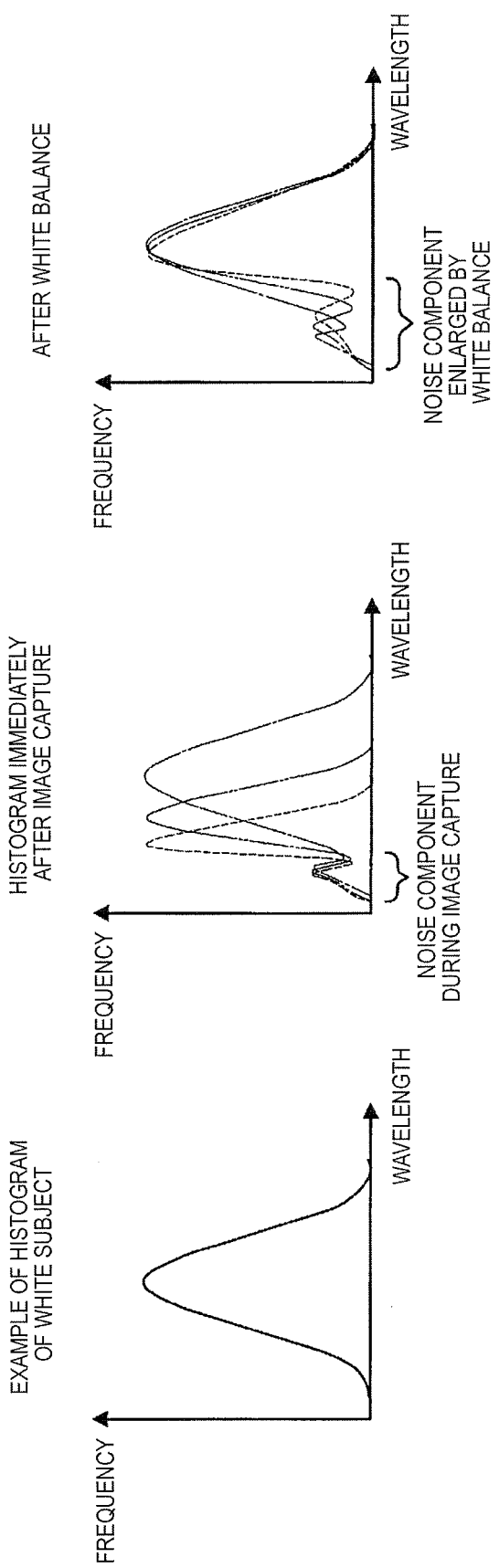

LIGHT SOURCE CONTROL DEVICE, METHOD OF CONTROLLING LIGHT SOURCE, AND IMAGE CAPTURE SYSTEM

TECHNICAL FIELD

The present disclosure relates to a light source control device, a method of controlling a light source, and an image capture system.

BACKGROUND ART

In the image capture systems such as endoscopic image capture devices, the single-plate image sensor exemplified by a Bayer structure has been recently employed to meet the demand for miniaturization of the device and for reduction in diameter of an insertion portion that is inserted into the body. The single-plate image sensor is more advantageous in that it is smaller in size than the three-plate image sensor employing a prism for spectrally dispersing light into a red component (R), a green component (G), and a blue component (B) or three image sensors.

The light source device of a type in which illumination light of different spectra is caused to emit on a time division basis in synchronization with image capture timing is known as the endoscopic image capture device employing such a single-plate image sensor. In one example, Patent Literature 1 discloses an image capture device that performs image capture using a frame sequential method by switching between a plurality of types of illumination light in synchronization with the image capture timing of a rolling shutter image sensor.

CITATION LIST

Patent Literature

Patent Literature 1: WO 2013/146311

DISCLOSURE OF INVENTION

Technical Problem

However, the image capture device disclosed in Patent Literature 1 is not designed to control the output of a light source depending on a result obtained by the image capture. Thus, in detecting color information of the red (R), green (G), and blue (B) components, the dynamic range of the image sensor fails to be used effectively. If the color information of each color is capable of being detected by effectively utilizing the dynamic range of the image sensor, it is possible to further improve the quality of an acquired image.

In view of this, the present disclosure provides a novel and improved light source control device, method of controlling the light source, and image capture system, capable of improving the quality of an acquired image by detecting each piece of color information of red (R), green (G), and blue (B) components to effectively utilize the dynamic range of the image sensor while using a single-plate image sensor.

Solution to Problem

According to the present disclosure, there is provided a light source control device including: a light source control unit configured to cause a plurality of narrowband light sources including at least a red light source, a green light source, and a blue light source to emit light on a time division basis; and a light quantity setting unit configured to set an output of each of the narrowband light sources on the basis of image information that is frame-sequentially detected by a monochrome single-plate image sensor configured to capture a reflected image of a subject illuminated with light emitted from the narrowband light source.

Further, according to the present disclosure, there is provided a method of controlling a light source, the method including: a step of causing a plurality of narrowband light sources including at least a red light source, a green light source, and a blue light source to emit light on a time division basis; a step of capturing a reflected image of a subject illuminated with light emitted from each of the narrowband light sources by a monochrome single-plate image sensor; and a step of setting an output of each of the narrowband light sources on the basis of image information detected by the single-plate image sensor.

Further, according to the present disclosure, there is provided an image capture system including: a plurality of narrowband light sources including at least a red light source, a green light source, and a blue light source; a light source control unit configured to cause the plurality of narrowband light sources to emit light on a time division basis; a monochrome single-plate image sensor configured to capture a reflected image of a subject illuminated with light emitted from the narrowband light source; a light quantity setting unit configured to set an output of each of the narrowband light sources on the basis of image information detected by the single-plate image sensor; and an image generation unit configured to generate a color image on the basis of a plurality of pieces of the image information captured in light emission of each of the narrowband light sources.

Advantageous Effects of Invention

According to the present disclosure as described above, it is possible to improve the quality of an acquired image by detecting each piece of color information of red (R), green (G), and blue (B) components to effectively utilize the dynamic range of the image sensor while using a single-plate image sensor. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 14 is a diagram illustrated to describe an increase in noise due to the white balance processing in related art.

MODE(S) FOR CARRYING OUT THE INVENTION

Figure 1:
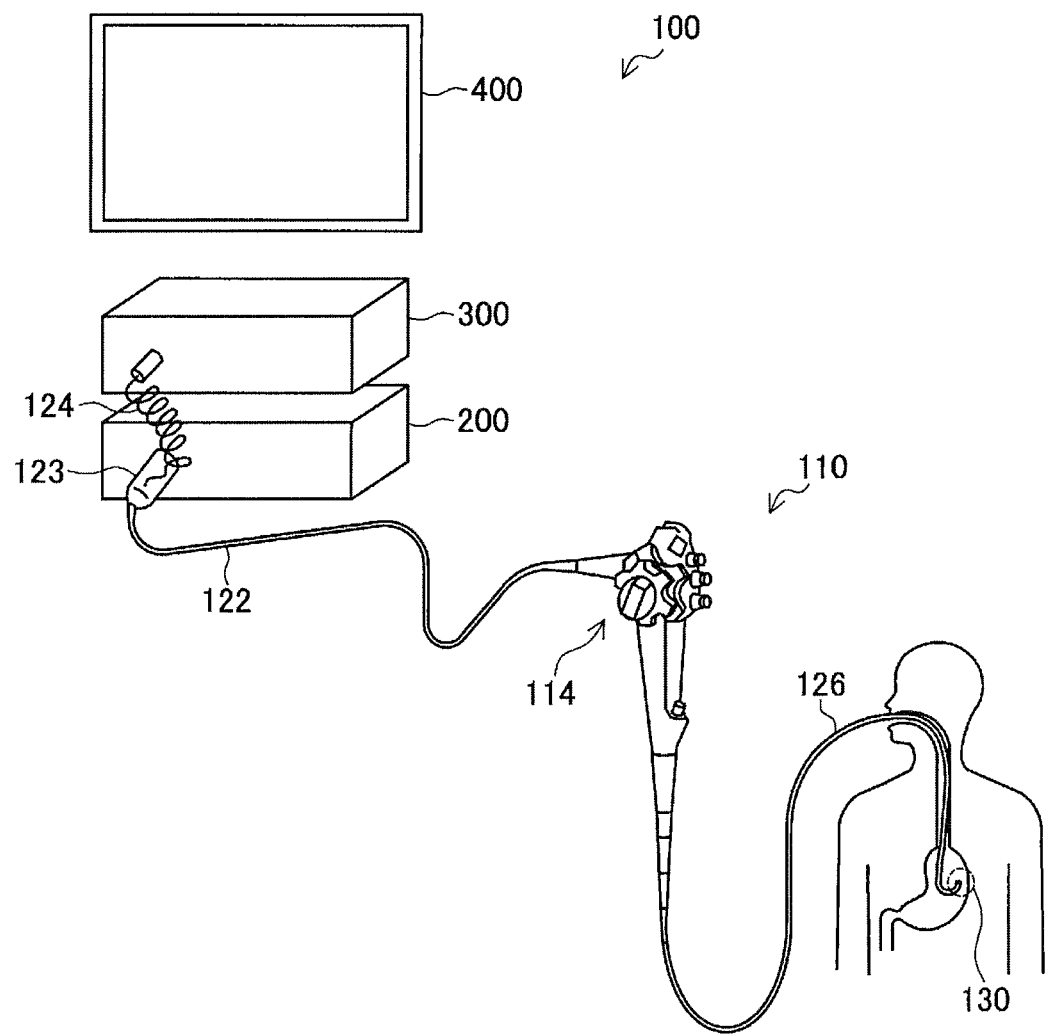
FIG. 1 is a schematic diagram illustrating an endoscopic image capture device according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will be given in the following order.
<1. Detailed description of background art>
<2. Image capture system>
(2.1. Overall configuration)
(2.2. Light source device)
(2.3. Image sensor)
(2.4. Image capture processing device)
(2.5. Light source control device)
<3. Processing of controlling image capture system>

Further, in this specification, "emitted light" refers to light emitted from each narrowband light source, and "illumination light" refers to light emitted from a light source device.

<1. Detailed Description of Background Art>

The background art of the present disclosure is now described in detail. In recent years, in a surgical image capture device exemplified by an endoscopic image capture device, the color image resolution has been changed from high vision to 4K, and the visibility of a diseased part has been improved. On the other hand, in the endoscopic image capture device used for the endoscopic diagnosis or surgery on the abdominal cavity, digestive organs, or the like, the reduction in diameter of a portion inserted into the body is being achieved to reduce the burden on patients and to improve the handling of surgical tools. The improvement in the resolution of an acquired color image is compromised with the reduction in diameter of a portion inserted into the body, and so it is desired to satisfy these demands concurrently. On the other hand, for the purpose of the reduction in size and diameter of the endoscopic image capture device, the image sensor used for the endoscopic image capture device is being shifted from a three-plate type to a single-plate type.

Figure 12:
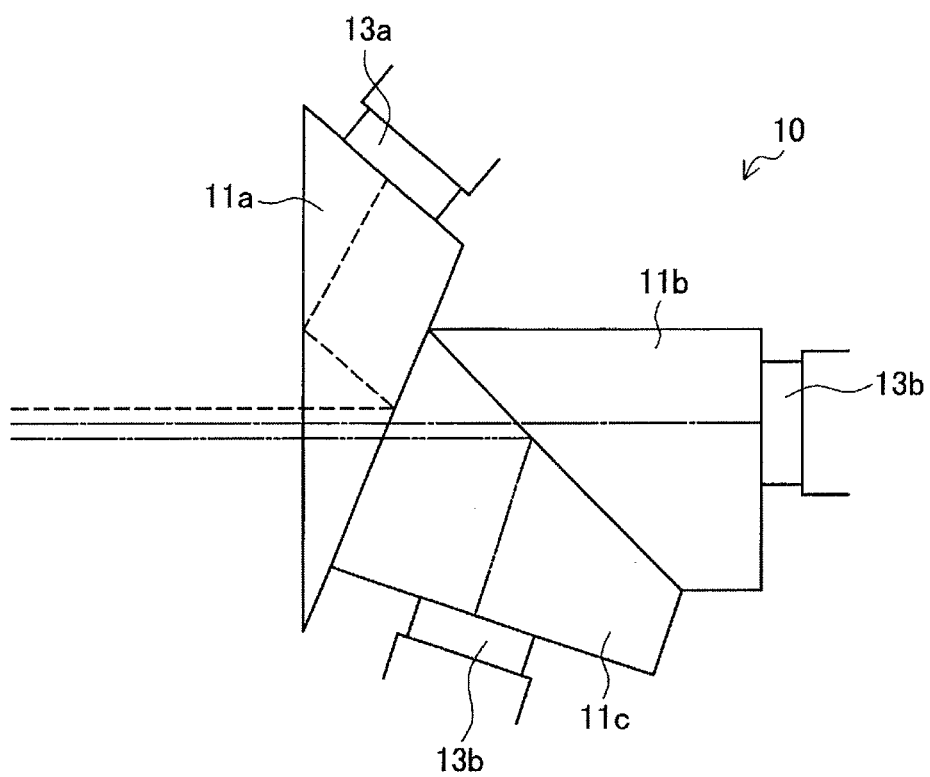
FIG. 12 is a diagram illustrated to describe a three-plate image sensor.

FIG. 12 is a schematic diagram illustrating an example of the configuration of a three-plate image sensor 10. The three-plate image sensor 10 is configured to include three dichroic prisms 11a, 11b, and 11c and two image sensors 13a, 13b, and 13c. In this three-plate image sensor 10, incident light is spectrally divided into a red component (R), a green component (G), and a blue component (B) by dichroic prisms 11a, 11b, and 11c, respectively, and light of each color component is received by each of the three image sensors 13a, 13b, and 13c, respectively. In this three-plate image sensor 10, although there is loss of light quantity at the dichroic prisms 11a, 11b, and 11c, it is possible to acquire color information of the red (R), green (G), and blue (B) components for each pixel, which leads to relatively optimal image quality.

Figure 13:
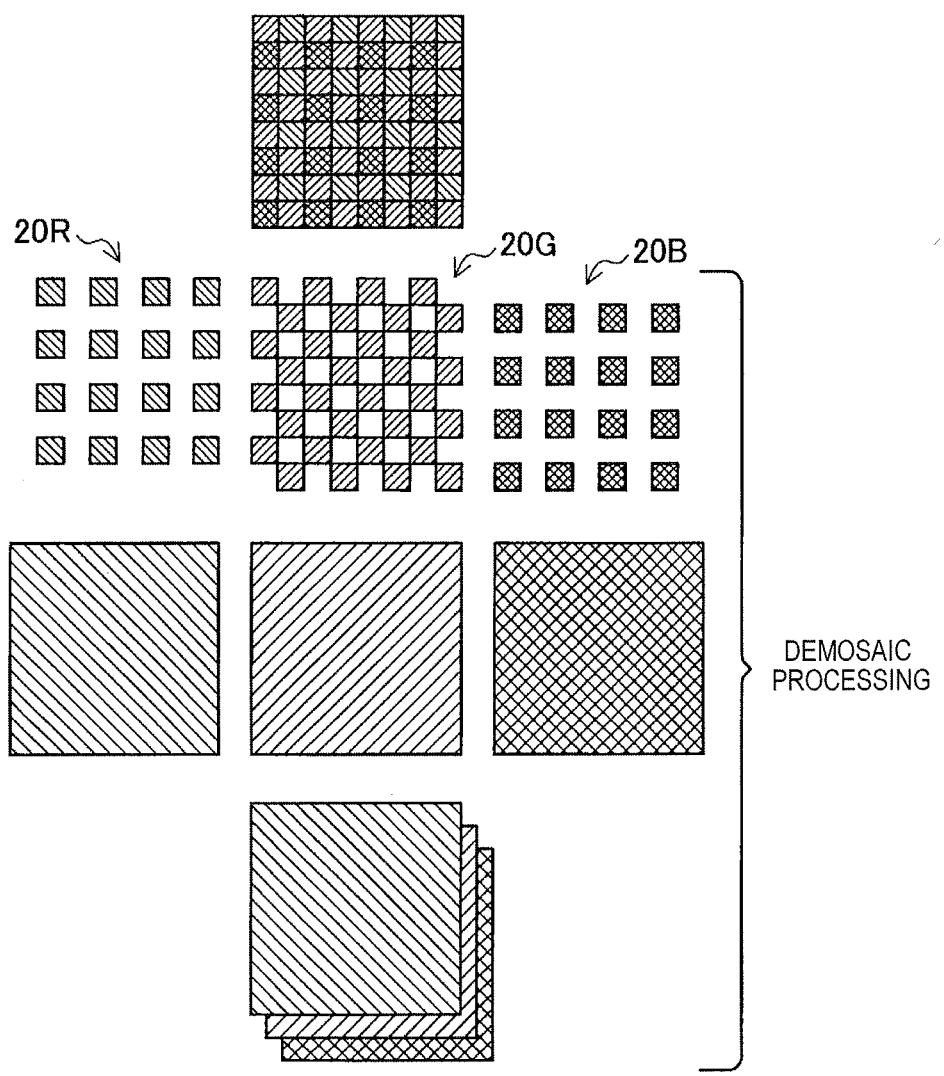
FIG. 13 is a diagram illustrated to describe demosaic processing by a single-plate image sensor having a Bayer structure.

FIG. 13 is a diagram illustrated to describe an overview of a single-plate image sensor having the Bayer structure. In the single-plate image sensor exemplified by the Bayer structure, respective color filters 20R, 20G, and 20B of R, G, and B are arranged for each pixel. In the illustrated example, the green color filter 20G is arranged in every other pixel in the row and column, and the red color filter 20R and the blue color filter 20B are arranged every other row for the remaining pixels.

In this single-plate image sensor, only one piece of the color information of red, green, and blue can be detected for each pixel, so interpolation processing called demosaicing, allows missing color information in each pixel to be predicted on the basis of color information of surrounding pixels and allows the images of the entire pixel region to be synthesized. In addition, although the single-plate image sensor having the Bayer structure has no loss of light quantity due to a dichroic prism like the three-plate image sensor, the loss of light quantity at the color filters 20R, 20G, and 20B is likely to occur. Thus, although the single-plate image sensor is advantageous from the point of miniaturization, its image quality tends to be lower than that of the three-plate image sensor.

In this regard, an example of the endoscopic image capture device includes a rigid endoscopic instrument and a flexible endoscopic instrument. The rigid endoscopic instrument is composed of an elongated optical system, which is mainly used for abdominal endoscopic surgery and is called a rigid endoscope, and an image sensor provided near the hand of the doctor. On the other hand, a flexible endoscopic instrument is mainly used for gastrointestinal examination or surgery, and has an image sensor that is typically placed at the tip of the endoscope. In the rigid endoscopic instrument, the portion of the rigid endoscope is narrow, so its optical resolution is limited. In the flexible endoscopic instrument, the size of the image sensor is limited, so its resolution is limited. In either of the rigid endoscopic instrument and the flexible endoscopic instrument, a single-plate image sensor having the Bayer structure is typically used.

As described above, in either of the rigid endoscopic instrument and the flexible endoscopic instrument, the resolution of an image that can be acquired using the image sensor is limited by the size of the optical system or the image sensor. In addition, in the case of the single-plate image sensor having the Bayer structure, the color information is interpolated by the demosaic processing, so the resolution tends to be further deteriorated.

Further, in the case where the color information of the red (R), green (G), and blue (B) components is captured at one time in either of the three-plate image sensor and the single-plate image sensor having the Bayer structure, the image capture is performed under the same exposure condition for each color component, but the image capture fails to be performed under the optimum exposure condition for each color component. On the other hand, in the case of a surgical image, a specific tendency is easily seen in the color component of the reflected image depending on a subject. In the surgical image, typically, the light quantity of the red component (R) and the green component (G) are large and the light quantity of the blue component (B) is small.

Furthermore, the configuration of the endoscopic image capture device is likely to cause the loss of image quality of the red component (R) to be increased in using the three-plate image sensor or the single-plate image sensor having the Bayer structure.

Thus, when the state of surgery is captured, dimming is performed with reference to the green component (G) that tends to cause the light quantity to be large in a captured image. In this case, the white balance is maintained by enlarging the luminance of the red (R) and blue (B) components by image processing after image capture and by increasing it to the same light quantity level as the green component (G). In other words, the red (R) and blue (B) components can have only a dynamic range of about ½ to ⅓ of the green component (G). Thus, the dynamic range of the image sensor fails to be used effectively for each color information of the red (R), green (G), and blue (B) components. It can be said that this case is similar to the case where each light source is caused to emit light on a time division basis by keeping the output of the light source constant for each color in performing the image capture.

On the other hand, in a case where the endoscopic image capture device is considered to be used as a surgical instrument, for the purpose of reducing heat generation of the illumination light itself or of reducing the burden on the internal organs such as drying and burning due to the illumination light, it is desirable to make the light quantity of illumination light as weak as possible. However, unlike the green component (G), as described above, the red (R) and blue (B) components are processed by enlarging their luminance by image processing, so noise tends to be conspicuous and it is difficult to reduce the light quantity of the entire illumination light. In particular, it is undesirable to enlarge the noise of the red component (R), which is important in the surgical image, by increasing the light quantity of the entire illumination light.

FIG. 14 is a diagram illustrated to describe that the noise of the red component (R) or the blue component (B) tends to be conspicuous. In FIG. 14, the histogram on the left shows the luminance value histogram of light in the reflected image of the white subject, and the histogram on the center shows the luminance value histogram for each of the red (R), green (G), and blue (B) components of light in performing image capture by the image sensor. In addition, in FIG. 14, the histogram on the right shows the luminance value histogram for each of the red (R), green (G), and blue (B) components after the adjustment of white balance by approximating the luminance value indicating the peak to the wavelength of the luminance value histogram of the white subject.

As illustrated in FIG. 14, the luminance value histogram of each of the red (R), green (G), and blue (B) components before the white balance adjustment shows similar noise component. On the other hand, in the luminance value histogram after enlarging the luminance of the red component (R) and the blue component (B) and performing the white balance adjustment, the noise components of the red component (R) and the blue component (B) are enlarged. In this way, the noise components of the red component (R) and the blue component (B) tend to be conspicuous, so it is necessary to prevent the decrease in the light quantity of the entire illumination light.

As described above, in the image capture system such as the endoscopic image capture device in related art, it is demanded to meet the requirements including the improvement of color image resolution, effective use of the dynamic range of an image sensor, and reduction of noise in an acquired image. The light source control device, the method of controlling a light source, and the image capture system according to the present disclosure are provided to meet these requirements.

<2. Image Capture System>
(2.1. Overall Configuration)

Figure 2:
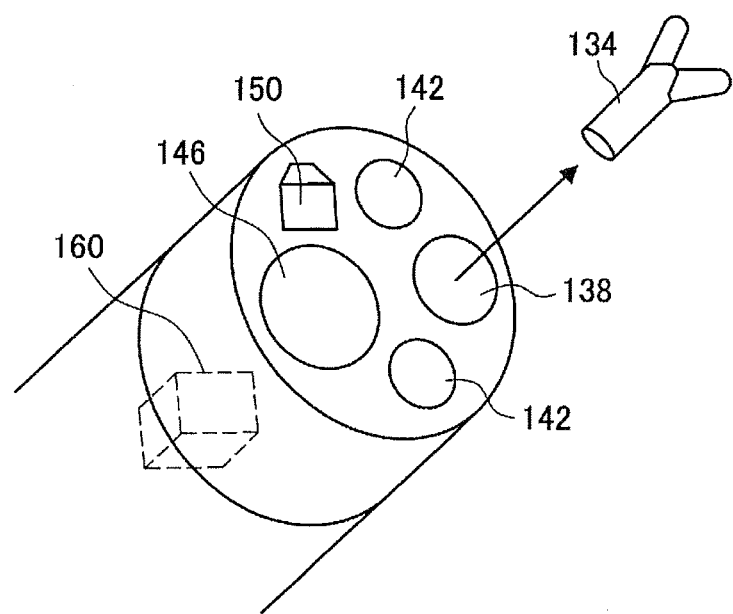
FIG. 2 is a schematic diagram illustrating a lens barrel of the endoscopic image capture device according to the present embodiment.

A schematic configuration of an image capture system according to a first embodiment of the present disclosure is now described. FIG. 1 is a schematic diagram of an endoscopic image capture device 100 serving as the image capture system according to the present embodiment. FIG. 2 is a diagram illustrated to describe a lens barrel portion 130 at the tip of an endoscope 110. The endoscopic image capture device 100 is configured to include the endoscope 110, a light source device 200, an image capture processing device 300, and a display device 400. The endoscopic image capture device 100 in the following description takes as an example a flexible endoscopic instrument having a portion that can be inserted into the body, but the portion that can be inserted into the body may be a rigid endoscopic instrument that has no flexibility.

The endoscope 110 is configured to include an elongated small-diameter insertion portion 126, an operation portion 114, and a universal cord 122 that is an electric cable. The universal cord 122 is connected to the light source device 200 via a connector 123. The light source device 200 supplies illumination light used to illuminate inside the body to the endoscope 110. The illumination light is supplied to the lens barrel portion 130 at the tip of the insertion portion 126 through the universal cord 122 and the insertion portion 126. A light guide (not illustrated), such as an optical fiber, is provided from the universal cord 122 to the lens barrel portion 130 at the tip of the insertion portion 126, and the illumination light is guided to the lens barrel portion 130. The insertion portion 126 has flexibility.

The lens barrel portion 130 is configured to include an illumination lens 142, an objective lens 146, a lens cleaning nozzle 150, a treatment tool insertion channel 138 through which a treatment tool 134 is installed, and an image sensor 160. The illumination light emitted from the light source device 200 illuminates the inside of the body through the illumination lens 142. The objective lens 146 is designed so that its focal point is a predetermined distance ahead of the lens barrel portion 130. The objective lens 146 may be configured to include a zoom mechanism and an automatic focus mechanism. A reflected image of a subject to which the illumination light is applied is detected by the image sensor 160 via the objective lens 146. The lens cleaning nozzle 150 discharges water or air for cleaning the objective lens 146.

Moreover, in the endoscopic image capture device 100, the light source device 200 is equipped with an air/water supply function (not illustrated) that discharges water or air from the lens barrel portion 130 at the tip of the insertion portion 126 of the endoscope 110.

The operation portion 114 is provided with an angle knob used to perform an operation for bending the tip of the insertion portion 126 or an operation switch for the endoscope function. The tip of the insertion portion 126 that includes the lens barrel portion 130 is bent by operating the angle knob. This changes the angle of an image capture position or the illumination direction. A coiled cable 124 extends from the connector 123, and the tip of the cable 124 is connected to the image capture processing device 300 via a connector or the like. The image information obtained by image capture in the image sensor 160 is processed by the image capture processing device 300 and the result is output to the display device 400. The display device 400 displays a captured image and other information in accordance with an input signal from the image capture processing device 300.

Figure 3:
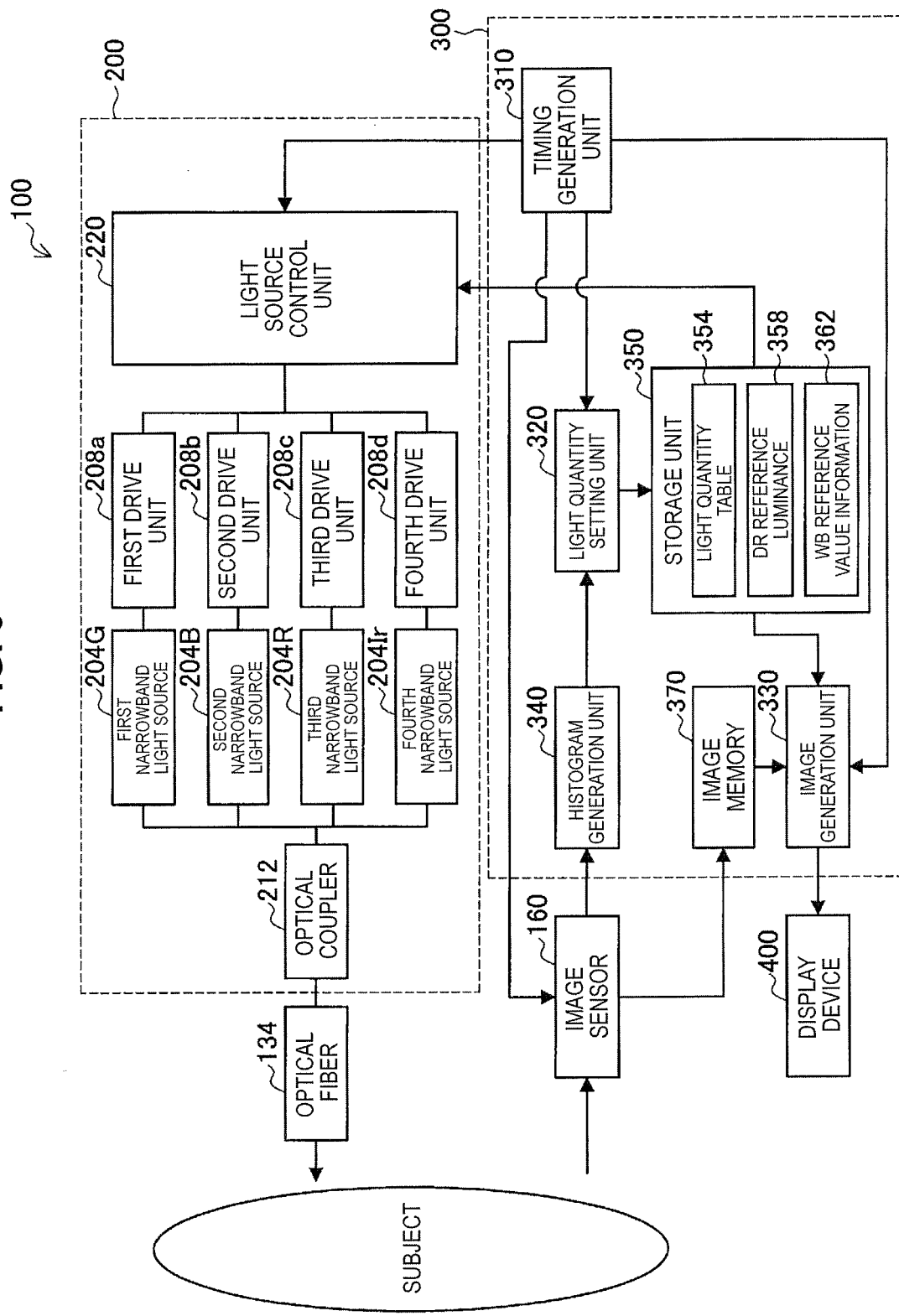
FIG. 3 is a block diagram illustrating the overall configuration of the endoscopic image capture device according to the present embodiment.

FIG. 3 is a block diagram illustrating the configuration of the endoscopic image capture device 100 illustrated in FIG. 12. The endoscopic image capture device 100 is configured to include the light source device 200, the image capture processing device 300, and the display device 400. The illumination light emitted from the light source device 200 illuminates the subject through an optical fiber 136 and an illumination lens (not illustrated). In addition, the image sensor 160 captures the reflected image from the illuminated subject, and outputs the image information to the image capture processing device 300. The endoscopic image capture device 100 according to the present embodiment is described below in detail with reference to FIG. 3.

(2.2. Light Source Device)

The light source device 200 is configured to include an optical coupler 212, a plurality of narrowband light sources, a plurality of drive units, and a light source control unit 220. The light source device 200 is configured to include a first narrowband light source 204G, a second narrowband light source 204B, a third narrowband light source 204R, and a fourth narrowband light source 204Ir. These narrowband light sources are light sources that emit light corresponding to a specific band, and include at least a red light source, a green light source, and a blue light source. In the present embodiment, an infrared light source (Ir) is provided in addition to a red light source (R), a green light source (G), and a blue light source (B). The following description will be given on the assumption that the first narrowband light source 204G is a green light source, the second narrowband light source 204B is a blue light source, the third narrowband light source 204R is a red light source, and the fourth narrowband light source 204Ir is an infrared light source.

The first narrowband light source 204G, the second narrowband light source 204B, the third narrowband light source 204R, and the fourth narrowband light source 204Ir are composed of, in one example, a semiconductor laser. The first narrowband light source 204G can also be composed of, in one example, a solid-state laser excited by the semiconductor laser. The output of each narrowband light source is electrically controllable. The number of narrowband light sources is not limited.

The optical coupler 212 is an optical multiplexer configured using a dichroic mirror or the like. The optical coupler 212 bundles the emitted light of the third narrowband light source 204R, the first narrowband light source 204G, the second narrowband light source 204B, and the fourth narrowband light source 204Ir, and guides the bundled light to the optical fiber 136 by using it as illumination light. The illumination light guided to the optical fiber 136 is transmitted to the lens barrel portion at the tip of the flexible scope to illuminate a target part.

Further, the light source device 200 is configured to include a first drive unit 208a, a second drive unit 208b, a third drive unit 208c, and a fourth drive unit 208d. These drive units can be driver circuits for driving the first narrowband light source 204G, the second narrowband light source 204B, the third narrowband light source 204R, and the fourth narrowband light source 204Ir, respectively. These drive units control a drive current of the narrowband light source on the basis of a drive command from the light source control unit 220.

The light source control unit 220 outputs a drive command to the first drive unit 208a, the second drive unit 208b, the third drive unit 208c, and the fourth drive unit 208d in accordance with a timing signal from a timing generation unit 310 of the image capture processing device 300. This allows the first narrowband light source 204G, the second narrowband light source 204B, the third narrowband light source 204R, and the fourth narrowband light source 204Ir to emit light on a time division basis.

Further, the light source control unit 220 controls the light quantity of each of the narrowband light sources in accordance with a light quantity signal that is set in a light quantity table 354 stored in a storage unit 350 of the image capture processing device 300. The light quantity signal may be, in one example, a control target value of the output of each narrowband light source. The light source control unit 220 is configured to include, in one example, a microprocessor, and performs the above-described processing by executing a software program stored in a memory unit (not illustrated).

(2.3. Image Sensor)

The image sensor 160 may be, in one example, a solid-state image sensor such as a charge-coupled device (CCD) or complementary metal-oxide-semiconductor (CMOS) image sensor. The image sensor 160 captures a reflected image of a subject illuminated with the illumination light via the objective lens 146. The image sensor 160 has a light receiving portion disposed at an image forming position of the objective lens 146, and the image sensor 160 captures the reflected image of the subject. In the present embodiment, the single-plate image sensor 160 corresponding to a monochrome imager is used as the image sensor 160.

The image sensor 160 captures a reflected image from the illuminated subject in accordance with the timing signal from the timing generation unit 310. Specifically, the timing generation unit 310 causes the first narrowband light source 204G, the second narrowband light source 204B, the third narrowband light source 204R, and the fourth narrowband light source 204Ir to emit light on a time division basis, and the image sensor 160 captures the reflected image for each light emission period of the narrowband light sources. This allows the image capture by the RGBIr frame sequential method to be performed. The image sensor 160 photoelectrically converts the captured reflected image to generate image information, and outputs the generated image information to the image capture processing device 300.

(2.4. Image Capture Processing Device)

The image capture processing device 300 is configured to include the timing generation unit 310, a light quantity setting unit 320, an image generation unit 330, a histogram generation unit 340, the storage unit 350, and an image memory 370. The image capture processing device 300 performs control processing on the basis of image information that is output from the image sensor 160 provided in the lens barrel portion 130 of the endoscope 110.

The storage unit 350 is a device used to store various data. The storage unit 350 is configured to include, in one example, some of a ROM, a RAM, a storage device, a removable recording medium, or the like. The storage device may be a magnetic storage device such as a hard disk drive (HDD), a semiconductor storage device, an optical storage device, or a magneto-optical storage device. In addition, the removable recording medium may be a CD or a DVD.

The timing generation unit 310 generates a timing signal indicating which of the narrowband light sources is caused to emit light, and outputs the timing signal to the light source control unit 220 of the light source device 200. In addition, the timing generation unit 310 outputs the timing signal to the light quantity setting unit 320, the image generation unit 330, and the image sensor 160. With this configuration, the light source device 200 is allowed to cause the plurality of narrowband light sources to emit light on a time division basis in accordance with the timing signal, and the image sensor 160 is allowed to perform image capture using the frame sequential method for light emitted from each narrowband light source. The timing generation unit 310 performs the above-described processing by executing the software program stored in the storage unit 350.

The histogram generation unit 340 generates a luminance value histogram of each captured image on the basis of the image information that is output from the image sensor 160. Information on the generated luminance value histogram is output to the light quantity setting unit 320. The histogram generation unit 340 performs the above-described processing by executing the software program stored in the storage unit 350.

The light quantity setting unit 320 determines the light quantity to be emitted from each narrowband light source on the basis of the information on the luminance value histogram generated by the histogram generation unit 340 and dynamic range (DR) reference luminance 358 stored in the storage unit 350. The timing signal from the timing generation unit 310 is input to the light quantity setting section 320, so the light quantity setting section 320 is able to recognize which luminance value histogram is obtained when the light emitted from the narrowband light source is illuminated, and to adjust the light quantity for each of the narrowband light sources. The determined light quantity is stored in the light quantity table 354 of the storage unit 350 as a value (a control target value) that is set for a new output of each narrowband light source. The light quantity setting unit 320 performs the above-described processing by executing the software program stored in the storage unit 350.

The image memory 370 stores the image information captured by the image sensor 160. The image memory 370 sequentially stores the image information that is output from the image sensor 160 and sequentially deletes old information exceeding the necessary number. As described above, the image sensor 160 is a monochrome image sensor, so the stored image information is information on a monochrome image irrespective of the color of the illumination light. The image memory 370 is composed of a semiconductor memory such as a RAM or a removable storage medium such as an HDD. The image memory 370 may be a component integrated with the storage unit 350.

The image generation unit 330 operates in accordance with the timing signal that is output from the timing generation unit 310. The image generation unit 330 reads the information on the necessary number of monochrome images stored in the image memory 370 and converts it into a color image. In this event, the image generation unit 330 performs white balance processing in accordance with white balance (WB) reference value information 362 stored in the storage unit 350. The image generation unit 330 causes the display device 400 to display the generated color image. The image generation unit 330 performs the above-described processing by executing the software program stored in the storage unit 350.

The storage unit 350 stores information on each of the light quantity table 354, DR reference luminance 358, and the WB reference value information 362. The light quantity table 354 is a control target value related to the setting of the light quantity when each narrowband light source is caused to emit light, and is updated on the basis of a result obtained by calculation in the light quantity setting unit 320. The DR reference luminance 358 is a value that is set on the basis of the dynamic range of the image sensor 160 and, in one example, can be set to a value corresponding to 0.9 in a case of normalizing the dynamic range from 0 to 1.0. This DR reference luminance 358 may be the same value for all the narrowband light sources corresponding to RGBIr, or may be set for each color on the basis of a desired color image depending on an observation target or the like.

Further, the WB reference value information 362 is used to set a correction value, which is used in performing white balance of a color image generated on the basis of acquired image information of light of each color. In the present embodiment, a light quantity correction coefficient L and a sensitivity correction coefficient S are stored as the WB reference value information 362. The light quantity correction coefficient L can be set as a proportion of a control target value, which is used in the case of causing each narrowband light source to emit light in a certain processing cycle, to a preset control reference value of each narrowband light source. The control reference value of each narrowband light source is appropriately set depending on the color image to be obtained. In addition, the sensitivity correction coefficient S can be set in advance as a reciprocal of the relative sensitivity (0 to 1.0) of the image sensor 160 to the light of each color emitted from each narrowband light source.

(2.5. Light Source Control Device)

Moreover, in the endoscopic image capture device 100 of the present embodiment, the functional components related to the control of the light source device 200 may be components of the light source control device according to the present disclosure. In other words, the light source control device according to the present disclosure is configured to include at least the light source control unit 220 and the light quantity setting unit 320. However, other components, that is, the timing generation unit 310, or all or some components of the storage unit 350 may be a component of the light source control device.

<3. Control Processing by Image Capture System>

Figure 4:
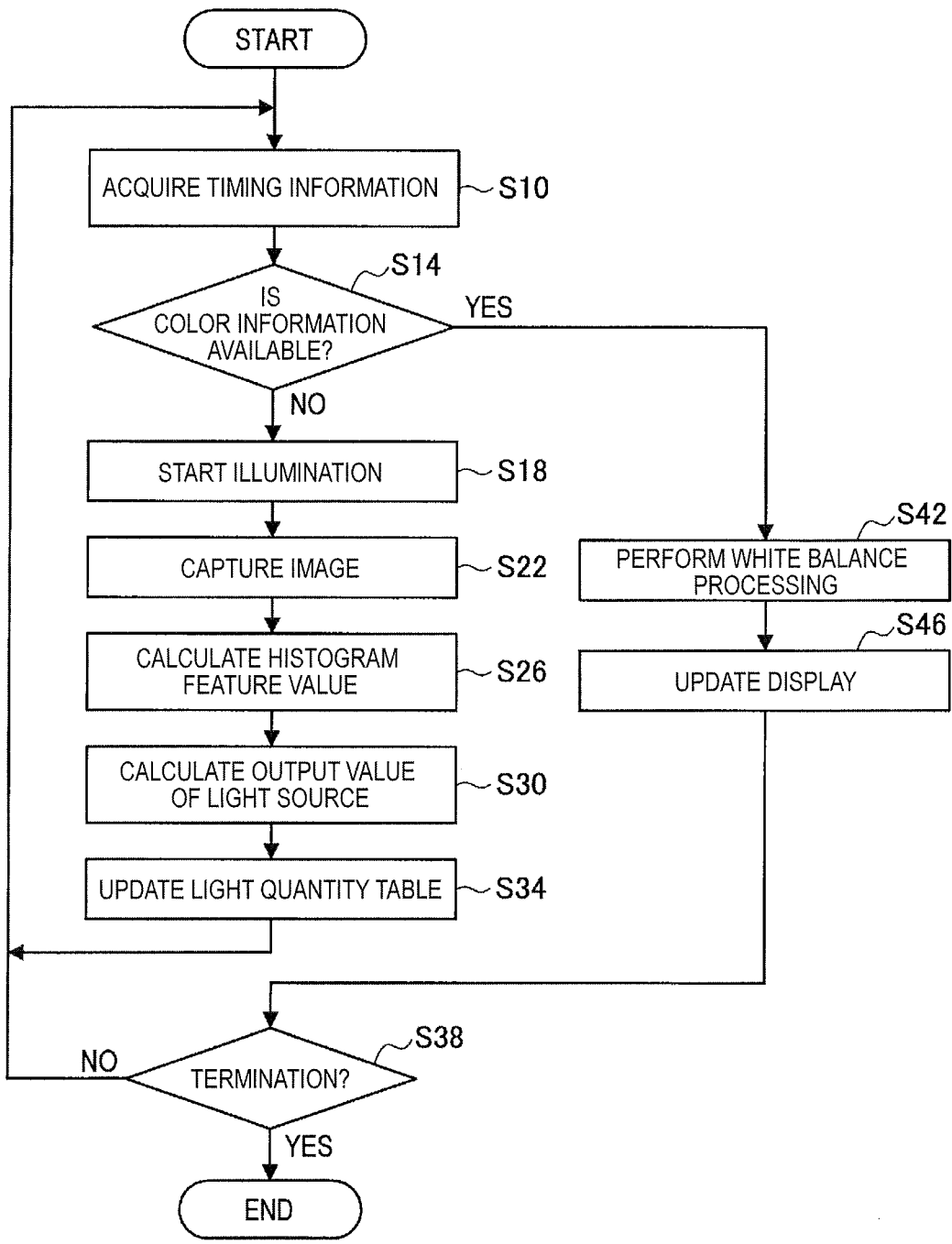
FIG. 4 is a flowchart illustrating processing of controlling the endoscopic image capture device according to the present embodiment.

An example of the overall configuration of the endoscopic image capture device 100 serving as the image capture system according to the present embodiment is described above. Next, an example of control processing by the light source device 200 and the image capture processing device 300 in the endoscopic image capture device 100 according to the present embodiment is described with reference to the flowchart illustrated in FIG. 4.

First, in step S10, the light source control unit 220 acquires timing information. The timing information includes information on which narrowband light source is caused to emit light and information on the light quantity of the narrowband light source. The information on which narrowband light source is caused to emit light is acquired on the basis of the timing signal that is output from the timing generation unit 310. In addition, the light source control unit 220 reads the light quantity table 354 stored in the storage unit 350, and acquires information on the control target value of the narrowband light source.

Figure 5:
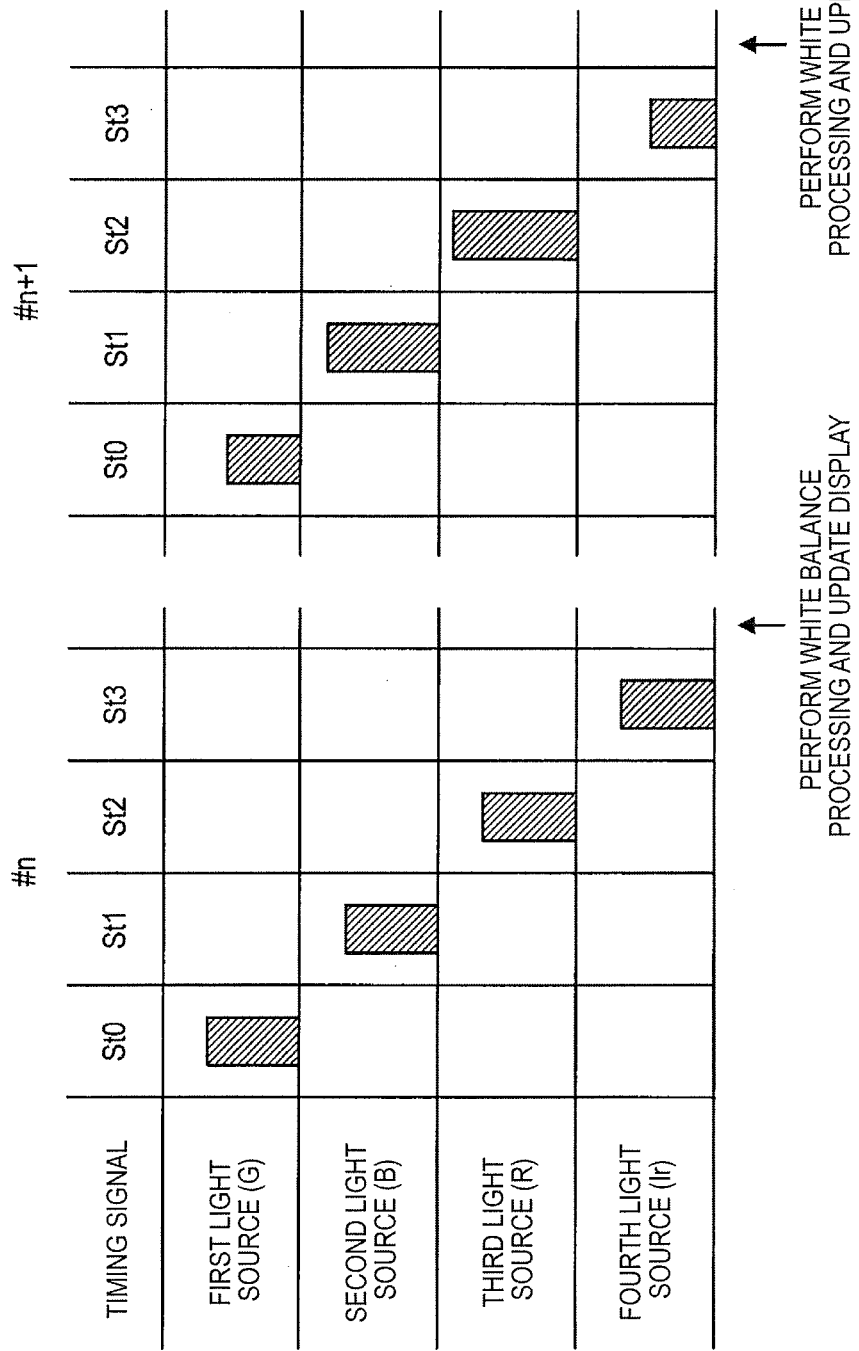
FIG. 5 is a diagram illustrated to describe timing signals and light quantity.

Here, FIG. 5 is a diagram illustrated to describe the timing signal and the light quantity of each narrowband light source, which are illustrated as timing information. In FIG. 5, the horizontal axis represents time. The hatched rectangular area in FIG. 5 indicates timing at which the first narrowband light source 204G, the second narrowband light source 204B, the third narrowband light source 204R, and the fourth narrowband light source 204Ir are caused to emit light and their light quantities. In other words, the horizontal width of the rectangular area indicates the light emitting period, and its height indicates the light quantity. The light quantity in the case of causing each narrowband light source to emit light corresponds to the control target value stored in the light quantity table 354 of the storage unit 350.

In each of the processing cycles #n and #n+1, the timing signals St0 to St3 sequentially generated by the timing generation unit 310 correspond to the timing signals of the first narrowband light source 204G, the second narrowband light source 204B, the third narrowband light source 204R, and the fourth narrowband light source 204Ir, respectively. In each of the processing cycles #n and #n+1, when the light emission of each narrowband light source in accordance with the timing signals St0 to St3 is completed, the white balance processing is performed and the display by the display device 400 is updated. The light quantities of the respective narrowband light sources in each of the processing cycles #n and #n+1 are adjusted on the basis of the image capture results obtained, in one example, in the preceding processing cycles #n−1 and #n.

In the example of FIG. 5, in the processing cycle #n, all the narrowband light sources emit light sequentially with the same light quantity and the white balance processing is performed, so the light quantity of each narrowband light source at the subsequent processing cycle #n+1 is adjusted. In other words, the height of each rectangular area in the processing cycle #n+1 is different from the height of each rectangular area in the immediately previous processing cycle #n. In this event, the light quantity is adjusted for each narrowband light source, so the height of the rectangular area in the processing cycle #n+1 differs for each narrowband light source.

With reference back to FIG. 4, in step S10, the light source control unit 220 acquires information on which narrowband light source and how much light quantity is caused to emit light, then, in step S14, determines whether information on all colors of RGBIr necessary for the image generation unit 330 to generate a color image is available. Here, acquisition of information on four colors of RGBIr is a single processing cycle, and it is determined whether information on all colors of RGBIr is available.

Figure 6:
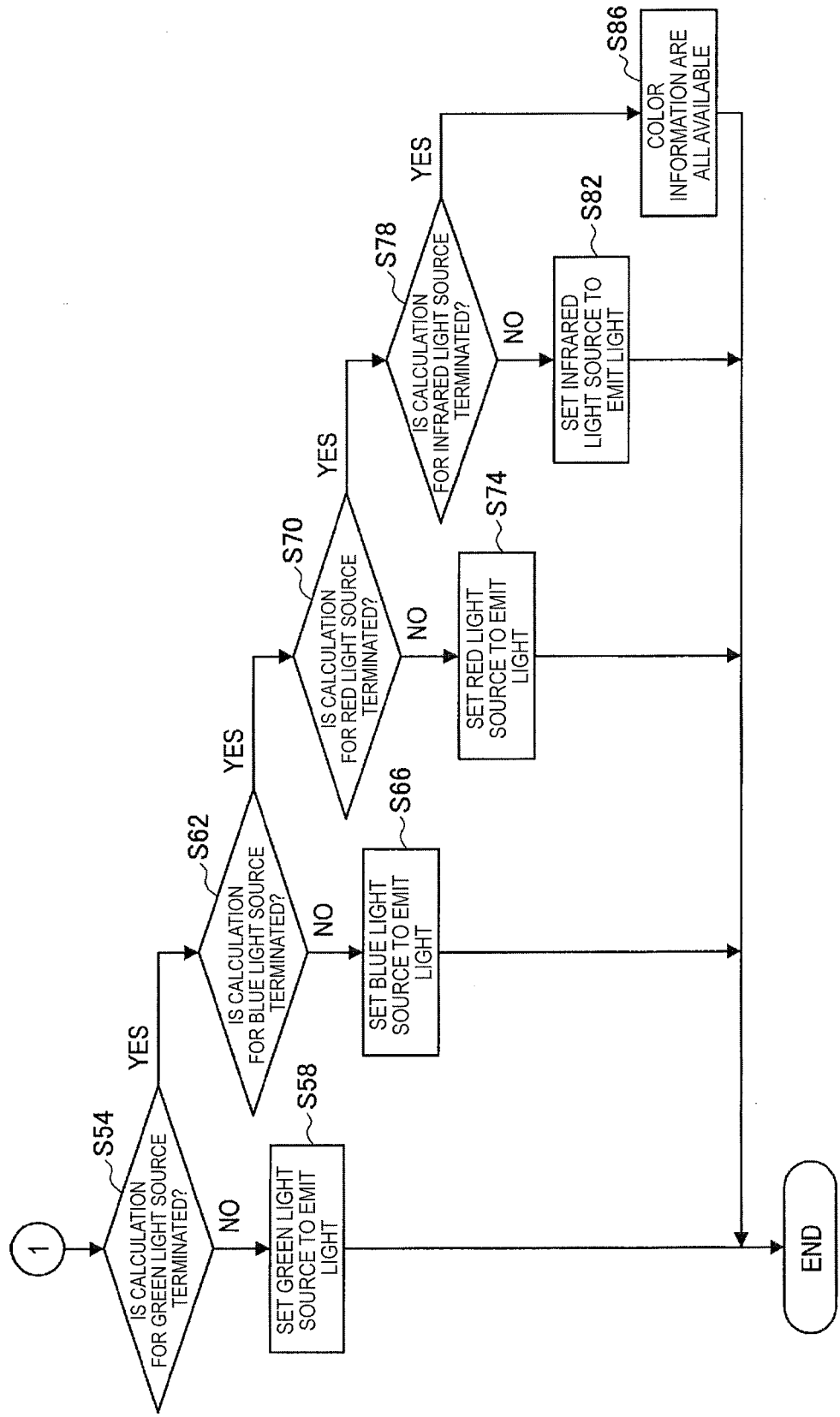
FIG. 6 is a flowchart illustrating determination of acquiring color information according to the present embodiment.

FIG. 6 is a flowchart illustrating an example of determination processing performed in step S14. In step S54, the light source control unit 220 determines whether information on the green light (G) corresponding to the first narrowband light source 204G is acquired. In one example, the light source control unit 220 may perform the determination on the basis of whether the light emission of the first narrowband light source 204G is completed in the present processing cycle. In addition, the light source control unit 220 may perform the determination on the basis of whether the control target value of the first narrowband light source 204G in the light quantity table 354 stored in the storage unit 350 is updated.

If the information on the green light (G) is not yet acquired (No in S54), in step S58, the light source control unit 220 sets the first narrowband light source 204G so that the first narrowband light source 204G emits light. On the other hand, if the information on the green light (G) is already acquired (Yes in S54), in step S62, the light source control unit 220 determines whether the information on the blue light (B) corresponding to the second narrowband light source 204B is required. In one example, the light source control unit 220 may perform the determination on the basis of whether the light emission of the second narrowband light source 204B is completed in the present processing cycle. In addition, the light source control unit 220 may perform the determination on the basis of whether the control target value of the second narrowband light source 204B in the light quantity table 354 stored in the storage unit 350 is updated.

If the information on the blue light (B) is not yet acquired (NO in S62), in step S66, the light source control unit 220 sets the second narrowband light source 204B so that the second narrowband light source 204B emits light. On the other hand, if the information on the blue light (B) is already acquired (Yes in S62), in step S70, the light source control unit 220 determines whether the information on the red light (R) corresponding to the third narrowband light source 204R is acquired. In one example, the light source control unit 220 may perform the determination on the basis of whether the light emission of the third narrowband light source 204R is completed in the present processing cycle. In addition, the light source control unit 220 may perform the determination on the basis of whether the control target value of the third narrowband light source 204R in the light quantity table 354 stored in the storage unit 350 is updated.

If the information on the red light (R) is not yet acquired (No in S70), in step S74, the light source control unit 220 sets the third narrowband light source 204R so that the third narrowband light source 204R emits light. On the other hand, if the information on the red light (R) is already acquired (Yes in S70), in step S78, the light source control unit 220 determines whether the information on the infrared light (Ir) corresponding to the fourth narrowband light source 204Ir is acquired. In one example, the light source control unit 220 may perform the determination on the basis of whether the light emission of the fourth narrowband light source 204Ir is completed in the present processing cycle. In addition, the light source control unit 220 may perform the determination on the basis of whether the control target value of the fourth narrowband light source 204Ir in the light quantity table 354 stored in the storage unit 350 is updated.

If the information on the infrared light (Ir) is not yet acquired (No in S78), in step S82, the light source control unit 220 sets the fourth narrowband light source 204Ir so that the fourth narrowband light source 204Ir emits light. On the other hand, if the information on the infrared light (Ir) is already acquired (Yes in S78), in step S86, the light source control unit 220 determines that information on all the colors is available.

With reference back to FIG. 4, except in the case where the information on all colors of RGBIr is available (No in S14), the light source control unit 220 causes one of the narrowband light sources to emit light and starts illumination in step S18. In this event, the light source control unit 220 outputs a drive command to the drive unit corresponding to the narrowband light source set in step S14 on the basis of the timing information acquired in step S10, and causes the narrowband light source to emit light with a predetermined light quantity for a predetermined time period. In addition, except in the case where information on all colors of RGBIr is available (No in S14), the image generation unit 330 does not update the color image.

Next, in step S22, the image sensor 160 captures a reflected image of a subject in accordance with the timing signals St0 to St3 that are output from the timing generation unit 310. Here, the image capture by the image sensor 160 is performed in synchronization with the light emission timing of the narrowband light source intended to emit light. The aperture stop or shutter speed in this case can be set to appropriate values in advance. In the control processing of the present embodiment, the light quantity of each narrowband light source is adjusted so that the dynamic range of the image sensor 160 can be effectively utilized. Thus, the image capture result obtained by effectively utilizing the dynamic range of the image sensor 160 can be achieved as long as there is no significant change in a subject.

The image sensor 160 outputs information on the captured image to the image capture processing device 300. The image information that is output to the image capture processing device 300 is stored in the image memory 370. In this event, the image information is deleted sequentially from the earliest stored one as occasion demands and it is replaced with new image information. This allows the image memory 370 to store the necessary number of pieces of image information. The stored image information is used for generation of a color image by the image generation unit 330. Thus, at least recently captured image information is stored in the image memory 370 for each narrowband light source.

Next, in step S26, the histogram generation unit 340 generates a luminance value histogram of the captured image on the basis of the image information captured by the image sensor 160. In addition, the histogram generation unit 340 calculates the control luminance of the narrowband light source, which is caused to emit light presently, on the basis of the generated luminance value histogram. This histogram generation unit 340 generates a luminance value histogram for each piece of image information of the narrowband light source captured by the image sensor 160 and calculates the control luminance of the narrowband light source. A specific example of determining the control luminance of the narrowband light source on the basis of the luminance value histogram is described below.

Figure 7:
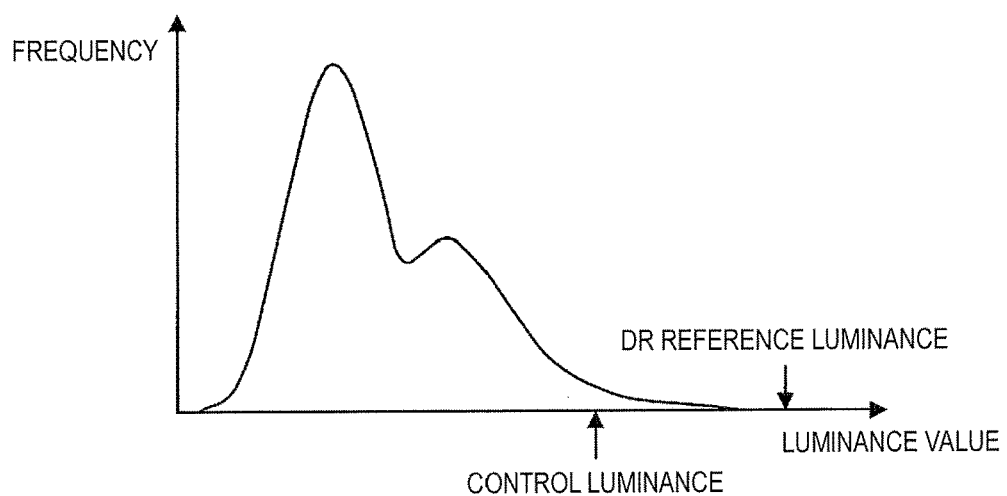
FIG. 7 is a diagram illustrated to describe a luminance value histogram.

FIG. 7 is a diagram illustrated to describe a luminance value histogram and control luminance of a certain narrowband light source. Here, the luminance or the luminance value is obtained by normalizing the dynamic range of the image sensor 160 between 0 and 1. In one example, in a case where the image sensor 160 has a 12-bit dynamic range, the luminance value of 1.0 corresponds to the pixel value of 4095 of the image sensor 160. In one example, in a case where the sum obtained by integrating the frequencies of the respective luminance values in the luminance value histogram is set to 100(%), the control luminance can be a luminance value at which the value obtained by integrating the frequency of each luminance value from the smaller luminance value becomes a predetermined ratio.

Although the luminance value at which the area becomes 100% indicates the maximum value of the captured pixels, in the actual image capture result, a high luminance value due to direct reflection may appear or an abnormal value due to failure of the image sensor 160 in units of pixels may also occur. Thus, it is preferable that the ratio of the area in the case of determining the control luminance is preferably a value smaller than 100%. Specifically, the ratio of the area is preferably set to a value of 95% or more and less than 100%. In addition, the ratio of the area may be set for each narrowband light source. In FIG. 7, in the case where the entire area of the luminance value histogram is set to 100(%), the luminance value at which the area having the smaller luminance value is 95(%) is defined as the control luminance.

Next, in step S30, the light quantity setting unit 320 calculates the output value (the control target value) of the narrowband light source that is caused to emit light presently. In the present embodiment, the light quantity setting unit 320 determines an increase/decrease ratio of the light quantity of the narrowband light source, which is caused to emit light presently, in accordance with the DR reference luminance 358 stored in the storage unit 350 by using the current control luminance calculated by the histogram generation unit 340. In one example, the increase/decrease ratio of the light quantity of a certain narrowband light source can be determined by Formula (1) below.

Increase/decrease ratio of light quantity=
(DR reference luminance−current control luminance)/current control luminance (1)

Then, the light quantity setting unit 320 integrates the increase/decrease ratio to the current control target value of the narrowband light source, and so sets the result as a new control target value of the narrowband light source. This allows the luminance of the image information corresponding to each color acquired in the subsequent processing cycle uniform, and so it is possible to reduce variations in noise for each color. In this event, in a case of determining a new control target value, a predetermined time constant may be added. This makes it possible to prevent the flicker phenomenon due to a drastic change in the light quantities of the narrowband light source.

Next, in step S34, the light quantity setting unit 320 updates the control target value of the narrowband light source, which is caused to emit light presently, in the light quantity table 354 stored in the storage unit 350 in accordance with the calculated new control target value. This allows the light quantity of light emitted from the narrowband light source to be adjusted in the subsequent processing cycle.

Each of the calculation processing in steps S18 to S34 described above is repeated until it is determined that the information on all colors of RGBIr is available in the determination of step S14. In other words, the calculation processing of steps S14 to S34 is performed for each processing cycle in the order of the first narrowband light source 204G, the second narrowband light source 204B, the third narrowband light source 204R, and the fourth narrowband light source 204Ir.

Then, in step S14, when the information on all colors of RGBIr is available (Yes in S14), in step S42, the image generation unit 330 executes the white balance processing of the image information acquired in the present processing cycle. In one example, the image generation unit 330 reads four pieces of image information corresponding to RGBIr stored in the present processing cycle from the image memory 370, and adjusts the white balance of the color image generated from the four pieces of image information by the following Formula (2).

[Math. 1]

$$\begin{pmatrix} R' \\ G' \\ B' \\ Ir' \end{pmatrix} = L * S * \begin{pmatrix} R \\ G \\ B \\ Ir \end{pmatrix} \qquad (2)$$

L: Light quantity correction coefficient
S: Sensitivity correction coefficient

[Math. 2]

$$L = \begin{pmatrix} Lr & 0 & 0 & 0 \\ 0 & Lg & 0 & 0 \\ 0 & 0 & Lb & 0 \\ 0 & 0 & 0 & Lir \end{pmatrix}, S = \begin{pmatrix} Sr & 0 & 0 & 0 \\ 0 & Sg & 0 & 0 \\ 0 & 0 & Sb & 0 \\ 0 & 0 & 0 & Sir \end{pmatrix}$$

In the present embodiment, the image generation unit 330 integrates the light quantity correction coefficient L and the sensitivity correction coefficient S with respect to the luminance of the image information by the illumination light of each color captured by the image capturing device 160, and aligns the gain of the luminance of each piece of image information.

In one example, the light quantity correction coefficient L (Lr, Lg, Lb, and Lir) may be obtained as a ratio of a reference control value appropriately set in advance to a current control target value of each narrowband light source that is set in the light quantity table 354. The integration of the light quantity correction coefficient L allows the luminance of the image information to be inversely corrected depending on the light quantity of the narrowband light source when each piece of image information is acquired, and the control luminance of each narrowband light source is made apparently to be constant.

The sensitivity correction coefficients S (Sr, Sg, Sb, and Sir) are coefficients used to eliminate the difference in sensitivity depending on the wavelength of light, which the image sensor 160 has. The sensitivity correction coefficient may be obtained as the reciprocal of the sensitivity of the image sensor 160 to the wavelength of each light in the case where the predetermined sensitivity is 100%. The integration of the sensitivity correction coefficient S allows the difference in luminance due to the difference in sensitivity of the image sensor 160 to be eliminated, and allows the image information to be corrected as if the image illuminated with the light of each color were captured with the sensitivity equivalent to each other.

Figure 8:
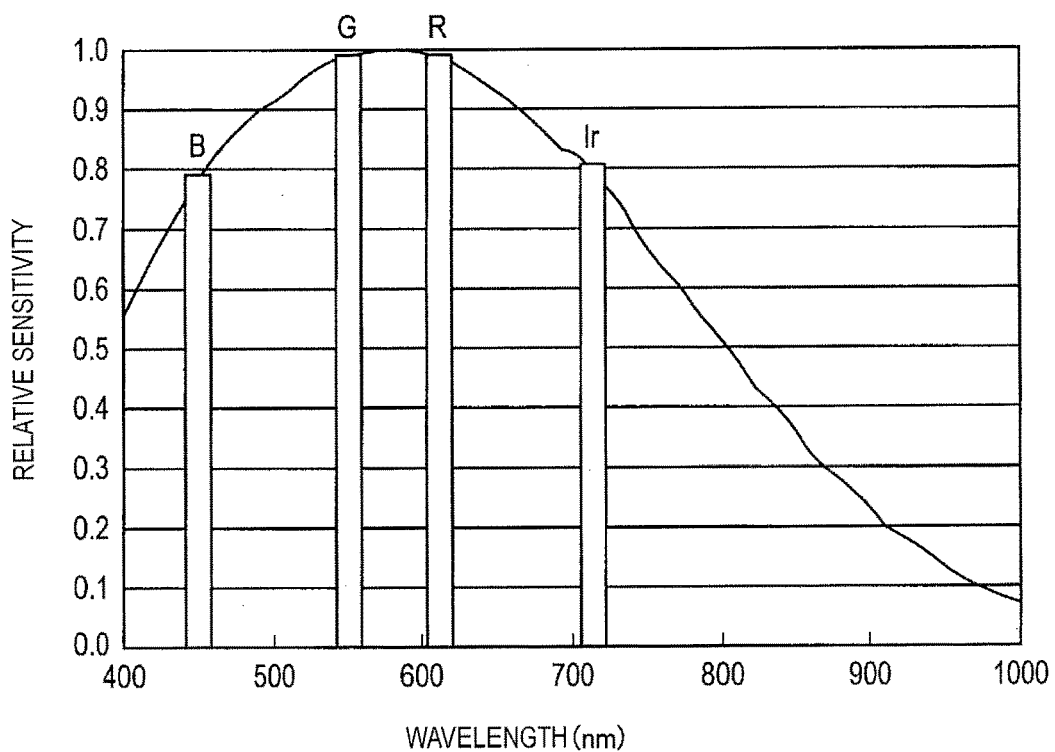
FIG. 8 is a diagram illustrated to describe sensitivity of an image sensor to a wavelength of light.

FIG. 8 is a diagram illustrated to describe a difference in sensitivity of the image sensor 160 depending on the wavelength of light. The horizontal axis represents wavelength, and the vertical axis represents relative sensitivity by the image sensor. In the present embodiment, although a single-plate image sensor 160 corresponding to a monochrome camera is used, such an image sensor 160 has spectral sensitivity characteristics as illustrated in FIG. 8. In the example illustrated in FIG. 8, relative sensitivity to red light (R) is 0.98, relative sensitivity to green light (G) is 0.99, relative sensitivity to blue light (B) is 0.8, and relative sensitivity to infrared light (Ir) is 0.82. In this case, the sensitivity correction coefficients S (Sr, Sg, Sb, and Sir) can be set to (1/0.98, 1/0.99, 1/0.8, and 1/0.82), respectively.

In step S42, the image generation unit 330 executes the white balance processing of the four pieces of image information, and then in step S46 the image generation unit 330 generates a color image on the basis of these four pieces of image information and displays it on the display device 400. This allows a color image, which is obtained by effectively utilizing the dynamic range of the image sensor 160 and is reduced in noise, to be displayed. In this event, linear matrix processing may be performed to change the color reproduction range or to change the overall color tone.

After updating the display, in step S38, the timing generation unit 310 determines whether to terminate the control processing. In one example, in the case where the operation of stopping the control processing is performed or it is in the mode of capturing a still image (Yes in S38), the control processing by the light source device 200 and the image capture processing device 300 are terminated. On the other hand, in the case where the control processing is not terminated (No in S38), the image capture result is displayed as a moving image by repeating the above-described procedures.

As described above, according to the endoscopic image capture device 100 according to the present embodiment, the control target value of each narrowband light source is adjusted so that the luminance of the image obtained by illuminating the emitted light of each narrowband light source approaches the DR reference luminance that is set depending on the dynamic range of the image sensor 160. Thus, in acquiring the image information corresponding to each color, it is possible to utilize effectively the dynamic range of the image sensor 160. Thus, it is possible for the endoscopic image capture device 100 to achieve the resolution equivalent to that of the three-plate image sensor by using the single-plate image sensor 160 corresponding to the monochrome camera. In this way, it is possible for the endoscopic image capture device 100 according to the present embodiment to improve the quality of the color image generated on the basis of each piece of image information, which leads to the reproduction of rich color information.

Further, the endoscopic image capture device 100 according to the present embodiment can obtain a high-resolution color image using the single-plate image sensor 160, and so it is possible to achieve a device that is smaller in size and diameter than the endoscopic image capture device in related art.

Further, in the endoscopic image capture device 100 according to the present embodiment, the control target value of each narrowband light source is adjusted in consideration of the DR reference luminance as described above. Thus, it is possible to cause each narrowband light source to emit light with the minimum necessary light quantity that can effectively utilize the dynamic range of the image pickup device 160.

Further, in the endoscopic image capture device 100 according to the present embodiment, the control target value of each narrowband light source is adjusted in consideration of the DR control luminance. Thus, it is possible to capture an image with uniform noise characteristics for each color without causing noise in the image of a specific color of RGBIr to be conspicuous.

Further, the endoscopic image capture device 100 according to the present embodiment corrects the image information corresponding to each color acquired by the image sensor 160 by using the predetermined light quantity correction coefficient L, and performs the white balance processing. Thus, it is possible to acquire the respective image information as if the light quantity of the narrowband light sources were illuminated with the same light quantity.

Furthermore, the endoscopic image capture device 100 according to the present embodiment corrects the image information corresponding to each color acquired by the image sensor 160 using the predetermined sensitivity correction coefficient S, and performs the white balance processing. Thus, it is possible to acquire the respective pieces of image information as if the respective pieces of image information corresponding to each color were captured with the sensitivity equivalent to each other. Thus, it is possible to further improve the quality of the obtained color image.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

In one example, in the above-described embodiment, although the narrowband light source is controlled using the luminance value histogram of the entire screen acquired by the image sensor 160, the present disclosure is not limited to this example. In the image capture system, the light quantity of the narrowband light source may be controlled by specializing in a more noticeable part of the observation target by using a result obtained by capturing a part of the acquired screen.

Figure 9:
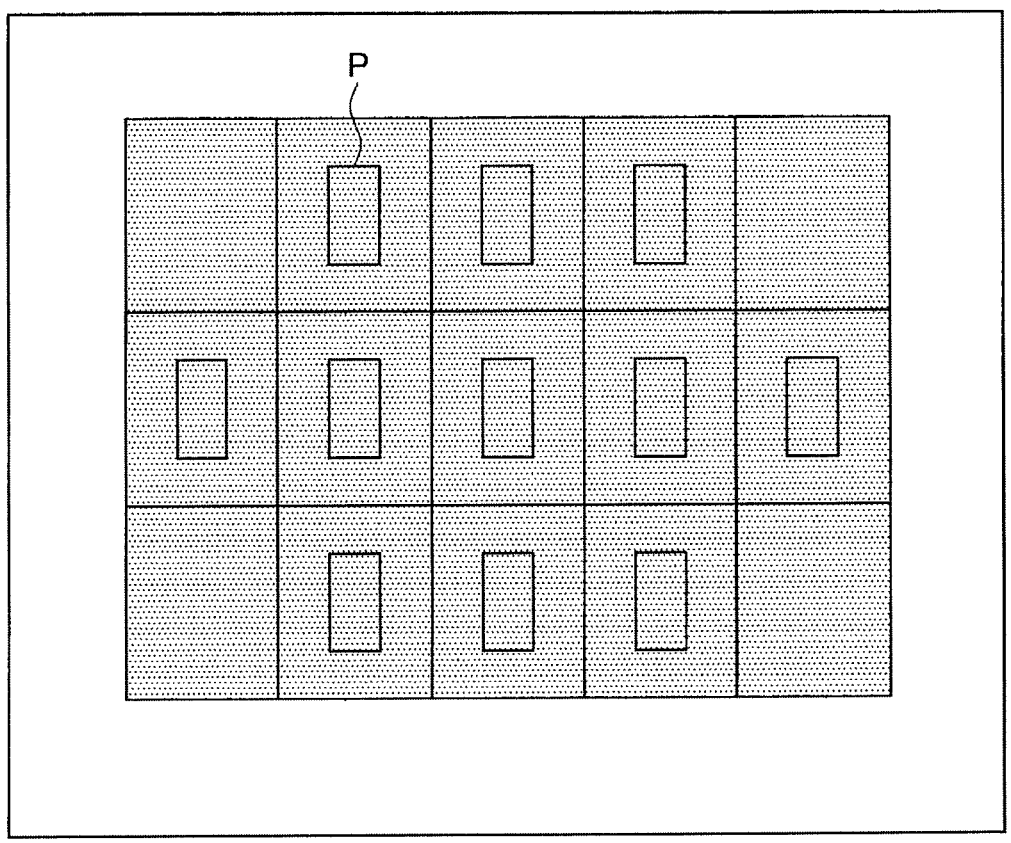
FIG. 9 is a diagram illustrated to describe a method of calculating control luminance during evaluation photometry.

Specifically, in the above embodiment, the luminance value at which the area of the smaller luminance value is 95(%) is set as the control luminance when the entire area of the luminance value histogram is 100(%). On the other hand, in one example, as illustrated in FIG. 9, in the case of performing evaluation photometry (division photometry) in which the screen is divided and the whole luminance is measured and the light quantity is adjusted based on the luminance, an average value of the luminance detected at a pixel P used for photometry may be used as the control luminance.

Figure 10:
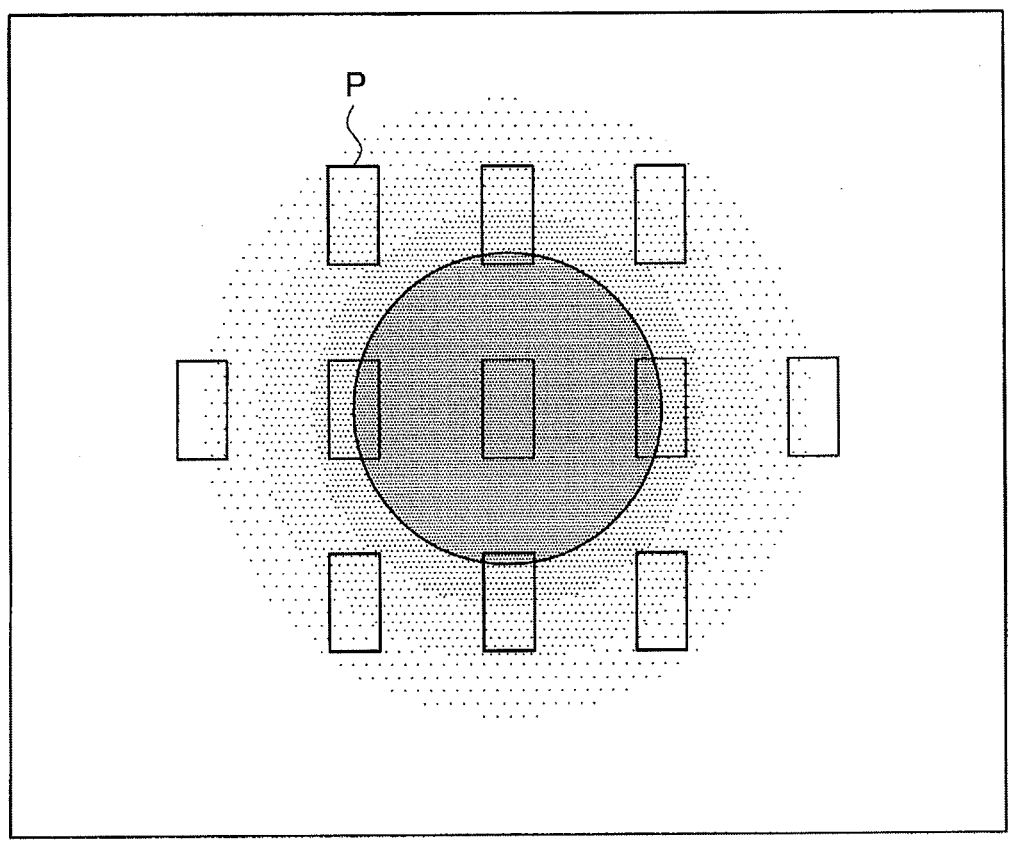
FIG. 10 is a diagram illustrated to describe a method of calculating control luminance during center-weighted average photometry.
Figure 11:
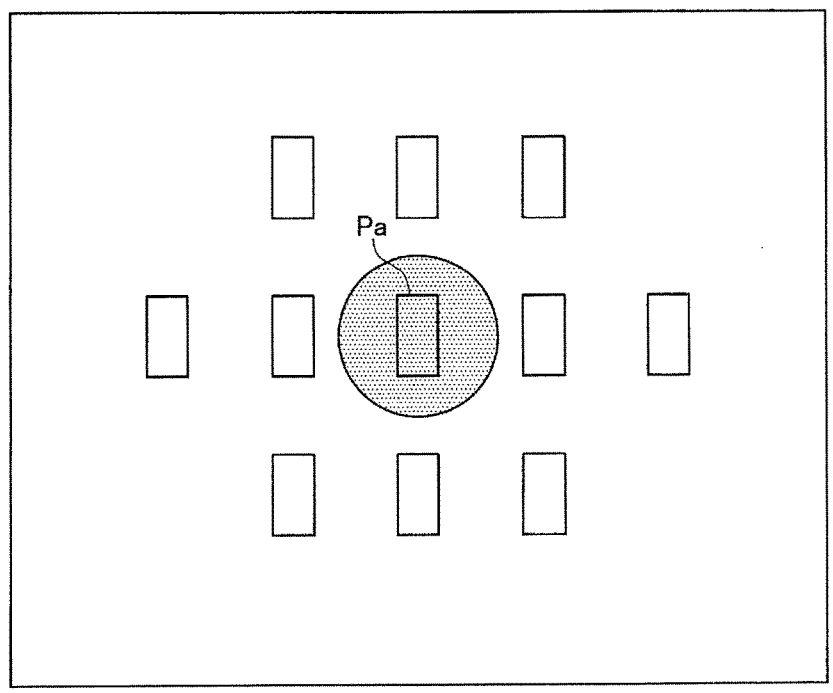
FIG. 11 is a diagram illustrated to describe a method of calculating control luminance during partial photometry.

Further, as illustrated in FIG. 10, in the case of performing center-weighted average photometry in which the photometry of the entire screen is averaged with an emphasis on the center of the screen, the luminance of each pixel P may be set, as the control luminance, a result obtained by weighting and averaging the central portion of the screen as the center. Furthermore, as illustrated in FIG. 11, in the case of performing partial photometry (spot photometry) for performing photometry of a particular part of the screen, an average value of luminance detected at one or a plurality of pixels Pa used for photometry may be used as the control luminance.

As described above, even in the case where the control luminance is determined on the basis of the result obtained by capturing a part of the screen acquired by the image sensor 160, it is possible to achieve the effect of the above-described embodiment, which leads to the improvement in the quality of a desired color image depending on the observation target.

Further, in the above embodiment, the DR reference luminance 358 is set to the luminance corresponding to 0.9 in the case of normalizing the dynamic range of the image sensor 160 from 0 to 1.0, but the DR reference luminance may be appropriately changed to an appropriate value. Further, in the case where the new control target value of each narrowband light source that is set using the set DR reference luminance 358 exceeds the controllable range of the narrowband light source, the DR reference luminance 358 may be changed to a smaller value with a predetermined ratio or with a predetermined width.

Further, the arrangement of a functional component or a storage unit that performs each control processing of the light source device 200 and the image capture processing device 300 described in the above embodiment is merely an example, and each functional component or storage unit may be provided on the other device. Furthermore, the light source device 200 and the image capture processing device 300 may be configured as a single device.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A light source control device including:

a light source control unit configured to cause a plurality of narrowband light sources including at least a red light source, a green light source, and a blue light source to emit light on a time division basis; and a light quantity setting unit configured to set an output of each of the narrowband light sources on the basis of image information that is frame-sequentially detected by a monochrome single-plate image sensor configured to capture a reflected image of a subject illuminated with light emitted from the narrowband light source.

(2)

The light source control device according to (1), further including:

a histogram generation unit configured to generate a luminance value histogram in the reflected image of the subject illuminated with the light emitted from each of the narrowband light sources on the basis of each piece of the image information that is frame-sequentially detected by the single-plate image sensor.

(3)

The light source control device according to (2), in which the light quantity setting unit sets the output on the basis of a current control luminance and a predetermined reference luminance for each of the narrowband light sources, the current control luminance being obtained on the basis of the luminance value histogram.

(4)

The light source control device according to (3), in which the light quantity setting unit increases or decreases the output on the basis of a difference between the current control luminance and the predetermined reference luminance.

(5)

The light source control device according to (3) or (4), in which the reference luminance is set on the basis of a dynamic range of the single-plate image sensor.

(6)

The light source control device according to any one of (3) to (5), in which, in a case where a newly set output of the narrowband light source exceeds a controllable range, the reference luminance is changed to a smaller value.

(7)

The light source control device according to any one of (3) to (7), in which the light quantity setting unit updates a control target value of the output stored in a storage unit for each of the narrowband light sources.

(8)

The light source control device according to any one of (3) to (7), in which the light quantity setting unit sets the output so that the control luminance of all the narrowband light sources approaches the same reference luminance.

(9)

The light source control device according to any one of (3) to (7), in which the reference luminance is set for each of the narrowband light sources.

(10)

A method of controlling a light source, the method including:

causing a plurality of narrowband light sources including at least a red light source, a green light source, and a blue light source to emit light on a time division basis;

capturing a reflected image of a subject illuminated with light emitted from each of the narrowband light sources by a monochrome single-plate image sensor; and setting an output of each of the narrowband light sources on the basis of image information detected by the single-plate image sensor.

(11)
An image capture system including:
a plurality of narrowband light sources including at least a red light source, a green light source, and a blue light source;
a light source control unit configured to cause the plurality of narrowband light sources to emit light on a time division basis;
a monochrome single-plate image sensor configured to capture a reflected image of a subject illuminated with light emitted from the narrowband light source;
a light quantity setting unit configured to set an output of each of the narrowband light sources on the basis of image information detected by the single-plate image sensor; and
an image generation unit configured to generate a color image on the basis of a plurality of pieces of the image information captured in light emission of each of the narrowband light sources.

(12)
The image capture system according to (11),
in which the image generation unit performs white balance processing by adjusting a gain of luminance of each piece of the image information on the basis of a ratio of a predetermined reference output to the output of each of the narrowband light sources during image capture.

(13)
The image capture system according to (11) or (12),
in which the image generation unit performs white balance processing by adjusting a gain of luminance of each piece of the image information on the basis of sensitivity of the single-plate image sensor to the light emitted from each of the narrow band light sources.

(14)
The image capture system according to (13),
in which the image generation unit adjusts the gain of the luminance of the image information by integrating a reciprocal of the sensitivity.

(15)
The image capture system according to any one of (11) to (14),
in which the image capture system is an endoscopic image capture device.

(16)
The image capture system according to any one of (11) to (15),
in which the plurality of narrowband light sources further include an infrared light source.

REFERENCE SIGNS LIST 100 endoscopic image capture device (image capture system)
160 image sensor
170 optical multiplexer
200 light source device
204G first narrowband light source
204B second narrowband light source
204R third narrowband light source
204Ir fourth narrowband light source
208a first drive unit
208b second drive unit
208c third drive unit
208d fourth drive unit
220 light source control unit
300 image capture processing device
310 timing generation unit
320 light quantity setting section
330 image generation unit
340 histogram generation unit
350 storage unit
370 image memory
400 display device

The invention claimed is:

1. A light source control device comprising processing circuitry configured to:
cause a plurality of narrowband light sources including at least a red light source, a green light source, and a blue light source to emit light on a time division basis; and
set an output of each of the narrowband light sources on the basis of a ratio of a number of luminance values that are smaller than or equal to a current control luminance value to a total number of the luminance values in a luminance value histogram as equal to a predetermined ratio corresponding to the respective narrowband light source, the luminance value histogram generated on the basis of image information that is frame-sequentially detected by a monochrome single-plate image sensor configured to capture a reflected image of a subject illuminated with light emitted from the respective narrowband light source.

2. The light source control device according to claim 1, wherein the processing circuitry is configured to:
for each of the narrowband light resources,
generate the luminance value histogram of the reflected image of the subject illuminated with the light emitted from the respective narrowband light source on the basis of the image information that is frame-sequentially detected by the single-plate image sensor, and
determine the current control luminance value on the basis of the luminance value histogram and the predetermined ratio corresponding to the respective narrowband light source.

3. The light source control device according to claim 2, wherein the processing circuitry is configured to:
set the output of each of the narrowband light sources on the basis of the current control luminance value and a reference luminance value of the respective narrowband light source.

4. The light source control device according to claim 3, wherein the processing circuitry is configured to:
increase or decrease the output of one of the narrowband light sources on the basis of a difference between the current control luminance value and the reference luminance value of the respective narrowband light source.

5. The light source control device according to claim 3, wherein the reference luminance values of the narrowband light sources are set on the basis of a dynamic range of the single-plate image sensor.

6. The light source control device according to claim 3, wherein, in a case where a newly set output of one of the narrowband light sources exceeds a controllable range, the reference luminance value of the one of the narrowband light sources is changed to a smaller value.

7. The light source control device according to claim 3, wherein the circuitry is configured to:
update a control target value of the output stored in a memory for each of the narrowband light sources.

8. The light source control device according to claim 3, wherein the processing circuitry is configured to:
set the output of the narrowband light sources so that the control luminance values of the narrowband light sources approach the same reference luminance value.

9. The light source control device according to claim 3, wherein the reference luminance value is set for each of the narrowband light sources.

10. A method of controlling a light source, the method comprising:
causing a plurality of narrowband light sources including at least a red light source, a green light source, and a blue light source to emit light on a time division basis;
capturing a reflected image of a subject illuminated with light emitted from each of the narrowband light sources by a monochrome single-plate image sensor; and
setting an output of each of the narrowband light sources on the basis of a ratio of a number of luminance values that are smaller than or equal to a current control luminance value to a total number of the luminance values in a luminance value histogram as equal to a predetermined ratio corresponding to the respective narrowband light source, the luminance value histogram generated on the basis of image information detected by the single-plate image sensor.

11. An image capture system comprising:
a plurality of narrowband light sources including at least a red light source, a green light source, and a blue light source;
a light source control unit circuit configured to cause the plurality of narrowband light sources to emit light on a time division basis;
a monochrome single-plate image sensor configured to capture a reflected image of a subject illuminated with light emitted from the respective narrowband light source;
a light quantity setting unit circuit configured to set an output of each of the narrowband light sources on the basis of a ratio of a number of luminance values that are smaller than or equal to a current control luminance to a total number of the luminance values in a luminance value histogram as equal to a predetermined ratio corresponding to the respective narrowband light source, the luminance value histogram generated on the basis of image information detected by the single-plate image sensor; and
an image generation unit circuit configured to generate a color image on the basis of the image information captured in light emission of each of the narrowband light sources.

12. The image capture system according to claim 11, wherein the image generation unit circuit is configured to perform white balance processing by adjusting a gain of luminance of the image information on the basis of a ratio of a predetermined reference output to the output of the respective narrowband light source during image capture.

13. The image capture system according to claim 11, wherein the image generation unit circuit is configured to perform white balance processing by adjusting a gain of luminance of the image information on the basis of sensitivity of the single-plate image sensor to the light emitted from the respective narrow band light source.

14. The image capture system according to claim 13, wherein the image generation unit circuit is configured to adjust the gain of the luminance of the image information by integrating a reciprocal of the sensitivity.

15. The image capture system according to claim 11, wherein the image capture system is an endoscopic image capture device.

16. The image capture system according to claim 11, wherein the plurality of narrowband light sources further include an infrared light source.

17. The method according to claim 10, further comprising:
for each of the narrowband light sources,
generating the luminance value histogram of the reflected image of the subject illuminated with the light emitted from the respective narrowband light source on the basis of the image information that is frame-sequentially detected by the single-plate image sensor; and
determining the current control luminance value on the basis of the luminance value histogram and the predetermined ratio corresponding to the respective narrowband light source.

18. The method according to claim 17, further comprising:
setting the output of each of the narrowband light sources on the basis of a difference between the current control luminance value and a reference luminance value of the respective narrowband light source.

19. The image capture system according to claim 11, further comprising:
a histogram generation unit circuit configured to
for each of the narrowband light sources,
generate the luminance value histogram of the reflected image of the subject illuminated with the light emitted from the respective narrowband light source on the basis of the image information that is frame-sequentially detected by the single-plate image sensor; and
determine the current control luminance value on the basis of the luminance value histogram and the predetermined ratio corresponding to the respective narrowband light source.

20. The image capture system according to claim 11, wherein the light quantity setting unit circuit is configured to set the output of each of the narrowband light sources on the basis of the current control luminance value and a predetermined reference luminance value for the respective narrowband light source.

* * * * *